United States Patent
Viot (10) Patent No.: US 10,695,450 B2
(45) Date of Patent: Jun. 30, 2020

(54) SYNTHESIS OF A RADIOACTIVE AGENT COMPOSITION

(71) Applicant: LABORATOIRES CYCLOPHARMA, Saint Beauzire (FR)

(72) Inventor: Gilles Viot, Beauregard Vendon (FR)

(73) Assignee: LABORATOIRES CYCLOPHARMA, Saint Beauzire (FR)

(*) Notice: Subject to any disclaimer, the term of this patent is extended or adjusted under 35 U.S.C. 154(b) by 0 days.

(21) Appl. No.: 15/219,745

(22) Filed: Jul. 26, 2016

(65) Prior Publication Data

US 2018/0028695 A1 Feb. 1, 2018

(51) Int. Cl.
| | | |
|---|---|---|
| A61K 51/04 | (2006.01) | |
| C07J 1/00 | (2006.01) | |
| C07J 71/00 | (2006.01) | |
| C07B 59/00 | (2006.01) | |
| C07B 63/00 | (2006.01) | |

(52) U.S. Cl.
CPC ........ *A61K 51/0493* (2013.01); *C07B 59/007* (2013.01); *C07B 63/00* (2013.01); *C07J 1/007* (2013.01); *C07J 71/0089* (2013.01); *C07B 2200/05* (2013.01)

(58) Field of Classification Search
CPC .. A61K 51/0493; A61K 51/04; C07B 59/007; C07B 63/00; C07B 2200/05; C07J 71/0089; C07J 1/007
See application file for complete search history.

(56) References Cited

U.S. PATENT DOCUMENTS

| | | | |
|---|---|---|---|
| 5,720,935 A | 2/1998 | Kassis et al. | |
| 7,238,338 B1 * | 7/2007 | Lu .................. | A61K 51/0491 424/1.11 |
| 7,264,792 B2 | 9/2007 | Gibson et al. | |
| 7,642,373 B2 | 1/2010 | Wadsworth et al. | |
| 7,977,361 B2 | 7/2011 | Collier et al. | |
| 7,985,422 B2 | 7/2011 | Vaya et al. | |
| 8,182,788 B2 | 5/2012 | Knight et al. | |
| 8,216,609 B2 | 7/2012 | Vaya et al. | |
| 8,354,092 B2 | 1/2013 | Kolb et al. | |
| 8,435,488 B2 | 5/2013 | Gill et al. | |
| 8,545,808 B2 | 10/2013 | Magneson et al. | |
| 8,658,132 B2 | 2/2014 | Nakamura et al. | |
| 8,865,122 B2 | 10/2014 | Gill et al. | |
| 9,388,125 B2 | 7/2016 | Purohit et al. | |
| 9,439,985 B2 | 9/2016 | Magneson et al. | |
| 9,682,927 B2 | 6/2017 | Purohit et al. | |
| 2005/0175536 A1 | 8/2005 | Knight Castro | |
| 2006/0039855 A1 | 2/2006 | Gibson et al. | |
| 2006/0292060 A1 | 12/2006 | Wadsworth et al. | |
| 2010/0056826 A1 | 3/2010 | Hayashi et al. | |
| 2010/0087959 A1 | 4/2010 | Williams, Jr. | |
| 2010/0196272 A1 | 8/2010 | Magneson et al. | |
| 2010/0221176 A1 | 9/2010 | Gill et al. | |
| 2010/0254902 A1 | 10/2010 | Van Den Bos | |
| 2010/0331292 A1 | 12/2010 | Dijcks et al. | |
| 2011/0182812 A1 | 7/2011 | Szardenings et al. | |
| 2011/0290381 A1 | 12/2011 | Kernig et al. | |
| 2012/0213700 A1 | 8/2012 | Magneson et al. | |
| 2012/0301399 A1 | 11/2012 | Nakamura et al. | |
| 2013/0149244 A1 | 6/2013 | Purohit et al. | |
| 2013/0216475 A1 | 8/2013 | Gill et al. | |
| 2013/0324715 A1 | 12/2013 | Wickstrom et al. | |
| 2014/0023586 A1 | 1/2014 | Magneson et al. | |
| 2014/0163368 A1 | 6/2014 | Rousso et al. | |
| 2015/0056136 A1 | 2/2015 | Cesati et al. | |
| 2015/0258099 A1 | 9/2015 | Hager et al. | |
| 2016/0347679 A1 | 12/2016 | Magneson et al. | |
| 2016/0362362 A1 | 12/2016 | Purohit et al. | |

FOREIGN PATENT DOCUMENTS

| | | | |
|---|---|---|---|
| FR | 3054445 | 2/2018 | |
| WO | WO 2010/078370 | * 7/2010 | ......... A61K 51/0455 |
| WO | WO-12082618 | 6/2012 | |
| WO | WO-12087908 | 6/2012 | |
| WO | WO-2012082618 | 6/2012 | |
| WO | WO-2012087908 | 6/2012 | |

OTHER PUBLICATIONS

Pharmimage, Jun. 2014, http://www.asn.fr/content/download/87701/612887/version/1/file/2_PHI+ASN+consultation+public+RN_DISTR+juin14.pdf . (Year: 2014).*
Knott et al., J. Label Compd. Radiopharm, 2011, 54, p. 749-753 (Year: 2011).*
Mori, et al., "Automatic synthesis of 16α-[$^{18}$F]fluoro-17β-estradiol using a cassette-type [$^{18}$F]fluorodeoxyglucose synthesizer", 2006, pp. 281-286, vol. 33, Nuclear Medicine and Biology.
Preliminary Search Report in corresponding French Application No. 1657163 dated May 12, 2017.
Written Opinion in Corresponding French Application No. 1657163 date.
Horne, et al, "Multi-Scale Modeling of the Gamma Radiolysis of Nitrate Solutions", Oct. 25, 2016, pp. 11781-11789, vol. 120, j. Phys. Chem B.
Sun et al, "Applications of Ionizing Radiation in Materials Processing" 2017, pp. 245, vol. 1, Institute of Nuclear Chemistry and Technology.
Bobrowski, et al, "Radiation Chemistry of Liquid Systems—Chapter 4", pp. 81-116.
Dzaugis, et al, "A quantitative model of water radiolysis and chemical production rates near radionuclide-containing solids", 2015, vol. 115, pp. 127-134, Radiation Physics and Chemistry.
Aita, et al, "Synthesis of high specific activity [18F]FDOPA using a synthesizing device with a user-configurable cassette", May 1, 2016, pp. 1-2, vol. 57, No. supplement 2 1812, J Nucl Med.
Yakabuskie, et al, "The Influence of Long-Term Gamma-Radiation and Initially Dissolved Chemicals on Aqueous Kinetics and Interfacial Processes", Jan. 2015, pp. 1-218, Electronic Thesis and Disseration Repository. 2669.
Radiolysis Process Modeling Results for Scenarios Used Fuel Disposition—prepared for US DOE, Jul. 2012.
Radiolysis Model Formulation for Integration with the Mixed Potential Model Fuel Cycle Research & Development—prepared for US DOE Jul. 10, 2014.

* cited by examiner

Primary Examiner — Michael G. Hartley
Assistant Examiner — Leah H Schlientz
(74) Attorney, Agent, or Firm — B. Aaron Schulman, Esq.; Stites & Harbison, PLLC (57) ABSTRACT

The present invention relates to a method for the synthesis of a radioactive agent composition comprising at least a purification step carried out in the presence of an antioxidant, to the composition obtained by this method comprising radioactive agent and excipient, and to the method for preventing radiolysis of radioactive agent composition comprising the synthesis of said radioactive agent according to the method of the invention.

19 Claims, 2 Drawing Sheets

SYNTHESIS OF A RADIOACTIVE AGENT COMPOSITION

The present invention relates to a method of synthesis of a radioactive agent comprising a radioactive halogen-labeled element.

More specifically, the present invention relates to a method for producing a radioactive agent, this method allowing inhibiting the radiolysis of the radioactive agent and allowing industrial-scale production. The present invention also relates to a composition obtained according to this method, and comprising a radioactive halogen-labeled compound, antioxidant and a low amount of ethanol.

Nuclear medicine allows patient examination, diagnosis and the treatment of diseases by administration of an agent containing a compound labeled with a specific radioactive isotope. The detection of the radiation emitted by such isotope allows obtaining a diagnosis by studying the medical imaging of these radiations.

Nuclear medicine imaging allows detection and treatment of various diseases and is generally more organ- or tissue-specific, allowing for instance localized cancers detection.

Different radioactive elements may be used according to the targeted receptors to image, for instance: $^{123}$I, $^{11}$C, $^{13}$N, $^{68}$Ga, or $^{18}$F. In particular, $^{18}$F-labeled compounds are well known and used in radiopharmaceutical industries.

Among $^{18}$F-labeled compounds one may cite [$^{18}$F]1-amino-3-fluorocyclobuthanecarboxylic acid ([$^{18}$F]-FACBC), [$^{18}$F]-fluorothymidine, [$^{18}$F]-fluorodeoxyglucose and [$^{18}$F]-fluoroestradiol ([$^{18}$F]-FES or FES). All these different radioactive fluoro-labeled compounds may be used in PET imaging.

In particular, [$^{18}$F]-fluoroestradiol or 16α-[$^{18}$F]fluoro-17β-estradiol is a radiotracer used in PET (positron emission tomography) imagery. [$^{18}$F]FES is used in particular for imaging estrogen receptors, which are an important prognostic factor for cancer, and especially breast cancer. [$^{18}$F] FES is a well-known radiotracer which has to be extemporaneously synthesized and thus implies a difficult process.

In order to undergo commercialization of such compound, it is required to store it in a concentrated solution. However, as most of radioactive compounds, [$^{18}$F]FES is subject to radiolysis when synthesized and the compound tends to decompose by self-radiation when it is too much concentrated.

Thus researches are carried out in order to stabilize this fluorine-labeled compound solution long enough to be administrated to a patient, before that the radiolysis occurred and damage the radioactive agent. In order to stabilize these compounds, it is known to add ethanol. However, in view of the application targeted, a high amount of ethanol may be detrimental.

The radiolysis prevention of fluorinated radioactive agents by adding an antioxidant such as ascorbic acid or ascorbic acid salt during the formulation step of the said compound is known from EP2119458 and EP2080526.

The addition of sodium ascorbate, after the synthesis and purification, to the final solution of the [$^{18}$F]FES to prevent radiolysis during storage is known from Mori et al. (Nuclear Medicine and Biology, 33 (2006) 281-286).

These processes described lead to decrease the radiolysis effect self-induced by the radioactive compound. However, these syntheses of a halogen-labeled radioactive compound imply to produce this compound only at a lab scale.

Indeed, industrial-scale production of fluoro-labeled compounds implies high quantity and/or high concentration of radioactive agent at several steps during the process. However, the more the radioactive agent is present in high quantity or highly concentrated, the more the radiolysis occurs. This phenomenon is especially encountered during the purification step which needs the concentration of the radioactive agent.

Depending on the synthesis process, ethanol is used at the end stage with quantities involved up to 15% or more by weight based on the total weight of the radioactive agent solution, which is a high transitional alcohol rate for patient. It is thus necessary to concentrate the solution to lower the concentration of ethanol. However, such concentration result in an increase of the radiolysis phenomenon and thus to a degradation of the radioactive agent, in particular [$^{18}$F]FES.

Ethanol may be evaporated during the synthesis, but this step may last a long time lapse which increases the synthesis length and also the volumetric activity. Following this evaporation step, the radioactive ingredient is highly and rapidly degraded by self-radiolysis. Indeed with the evaporation, the active ingredient is more concentrated and thus the induced radiolysis is accordingly more important.

The present invention has been made in view of the above circumstances, by aiming to industrially produce the radioactive agent such as [$^{18}$F]FES, in such a way that the compound may be produced in high quantity and high concentration and that the ethanol proportion is acceptable for beings and thus does not require evaporation of the final product.

The present invention relates to a method for the synthesis of a radioactive agent composition comprising at least a purification step carried out in the presence of an antioxidant. The present invention aims to prevent and inhibit the radiolysis of the radioactive agent and enhancing its stability during and after the synthesis in a better way that with the methods described in the background art. This stabilization of the radioactive agent is possible thanks to the addition of an antioxidant during the purification step of the method.

Any radioactive agent may be prepared with the method of the invention. In a preferred embodiment, the radioactive agent is a halogen-labeled agent, and preferably the radioactive agent is a fluoro-labeled agent.

According to the invention, the method comprises the following steps:
i) Radioelement synthesis from 18-oxygen enriched water in order to get $^{18}$F$^-$,
ii) Radiolabeling of a compound precursor with $^{18}$F$^-$ obtained at step i);
iii) Purification of the radio-labeled compound obtained at step ii).

The purification step iii) is made in the presence of an antioxidant.

Preferably, the radioactive fluoro-labeled agent may be, but is not limited to, [$^{18}$F]-fluoroestradiol ([$^{18}$F]FES).

[$^{18}$F]-fluoroestradiol or 16α-[$^{18}$F]fluoro-17β-estradiol is a radiotracer especially used in PET (positron emission tomography) imaging represented by formula (I).

[$^{18}$F]FES is used for imaging estrogen receptors, which is an important prognostic factor for cancer, and especially breast cancer.

According to the invention, the method is preferably applied to produce [$^{18}$F]FES and thus preferably comprises the following steps:

i) Radioelement synthesis from 18-oxygen enriched water in order to get $^{18}$F$^-$, ii) Radiolabeling of [$^{18}$F]FES precursor with $^{18}$F$^-$ obtained at step i);

iii) Purification of crude [$^{18}$F]FES obtained at step ii) in the presence of an antioxidant;

The method of the invention refers to the synthesis of a radioactive agent. Thus, all the different steps preferably have to be carried out in a lead shielded box, ventilated in class C.

The different steps of the method of the invention are preferably carried out in an automatic cassette-type synthesizer.

Synthesis steps of the method will be now described in details.

i) Radioelement Synthesis

Fluorine-18 is a radioelement which half-time life is about 110 min. This compound has to be prepared extemporaneously to be used in the synthesis.

Fluorine-18 is generally prepared by high energy protons bombardment according to the $^{18}$O(p,n)$^{18}$F nucleophilic substitution reaction. This reaction is carried out in a cyclotron. The energy of the protons used for irradiation is generally comprised between 11 and 18 MeV.

Oxygen-18 is obtained from enriched water. Enriched water of at least 85% $^{18}$O enrichment may be used. For instance, enriched water from CIL®, ROTEM® or ORPHACHEM® companies may be used.

ii) Radiolabeling

Radiolabeling is a nucleophilic substitution reaction preferably carried out in anhydrous media. Any anhydrous solvent may be used, and preferably, acetonitrile is used.

18-fluoride obtained at step i) is preferably fixed on an anion-exchange resin which allows to get rid of the water and radionuclidic impurities.

Then, 18-fluoride is eluted by a tetrabutylammonium (TBA) carbonate solution or a Kryptofix222/potassium carbonate solution, and thus forms a neutralized complex with TBA or K222/K+ which has nucleophilic properties and acts as a phase-transfer catalyst. Preferably, TBA carbonate solution is used.

The eluate is then transferred into the reactor and preferably dry-evaporated under dry nitrogen at a temperature comprised between 80 and 120° C., preferably between 90 and 100° C.

In a preferred embodiment, the temperature of evaporation is equal to 95° C.

Preferably, acetonitrile is added to form an azeotrope with water and favor the total desiccation.

The precursor is any compound which may react with 18-fluoride-TBA or 18-fluoride-K222/K+ complex to give the desired radioactive agent. For example, 3-O-methoxymethyl-16,17-O-sulfuryl-16-epiestriol represented by formula (II) is preferably used as [$^{18}$F]FES precursor.

(II)

The precursor, in anhydrous solution of a solvent, preferably acetonitrile (CH$_3$CN) is added into the reactor to react with 18-fluoride-TBA or 18-fluoride K222/K+ complex by nucleophilic substitution.

Temperature is preferably raised to a temperature at least equal to 100° C. Preferably the temperature is comprised between 100 and 140° C., advantageously between 120 and 140° C.

In a preferred embodiment, the temperature is preferably equal to 130° C.

In a preferred embodiment, radiolabeling temperature is maintained in the reactor during 5 to 20 min, preferably during 10 min.

Optionally, acidic hydrolysis may be carried out to deprotect functions of the precursor.

For example, in the [$^{18}$F]FES synthesis, acidic hydrolysis is carried out in order to deprotect the ester function formed in 17β, the hydroxyl function in C3 and the cyclic sulfate still present on the residual precursor.

Different acidic hydrolysis may be carried out. Hydrochloric acid may be used but the hydrolysis is slow and non-total.

In a preferred embodiment of the invention, sulfuric acid is used leading to a hydrolysis step fast and total. Preferably, H$_2$SO$_4$ is solubilized in ethanol.

Hydrolysis step is preferably carried out under a temperature comprised between 90 and 130° C., preferably at 110° C.

Hydrolysis step is preferably carried out during between 2 and 20 min, preferably, during 5 min.

Crude radioactive agent, preferably [$^{18}$F]FES, is obtained at the end of this step.

iii) Purification

According to the present invention, step iii) consists in the purification of the crude solution obtained at step ii). As mentioned above, this step is carried out in the presence of an antioxidant. Preferably, the antioxidant is added in solution, preferably in aqueous solution.

Different methods of purification known by the skilled person in the art may be used in order to carry out this step, such as: evaporation, use of semi-preparative High Pressure Liquid Chromatography (HPLC) or reversed-phase cartridge, these methods being used alone or in a combination.

High concentrations of [$^{18}$F]FES in solution induce severe radiolysis of the radioactive component.

According to the invention, an antioxidant is added during the purification step in order to stabilize the radioactive agent formed at step ii) and inhibit radiolysis.

The concentration of the solution of antioxidant added during the purification step is at least equal to 0.1% m/v, preferably the concentration of the solution of antioxidant is comprised between 0.45% and 0.55% m/v, and preferably the concentration of the solution is equal to 0.5% m/v.

In a preferred embodiment according to the invention, the purification step consists of one to three different and successive purifications chosen among purification carried out on a reversed-phase cartridge, and purification carried out on HPLC.

Preferably, the purification step consists of two different purification steps, namely purification carried out on a reversed-phase cartridge and purification carried out on HPLC.

Preferably, the purification step consists of three different purification steps, preferably the purification step consists of the three following successive purification steps: purification on a reversed-phase cartridge, purification on HPLC and purification on a second reversed-phase cartridge.

In a preferred embodiment according to the invention, antioxidant is preferably added during at least one of the three purification steps.

In a preferred embodiment, antioxidant is added during the purification step by HPLC.

In a preferred embodiment according to the invention, the antioxidant is added during the three purification steps.

In a preferred embodiment according to the invention, the antioxidant is added in solution, preferably in an aqueous solution.

The concentration of the solution of antioxidant added during the purification step is at least equal to 0.1% m/v, preferably the concentration of the solution of antioxidant is comprised between 0.45% and 0.55% m/v. Preferably, the concentration of solution of antioxidant is equal to 0.5% m/v with respect to water content of solution.

Preferably, the mass ratio of the antioxidant with respect to the 18-fluorine used during the synthesis is about equal to 5000.

Preferably, the purification step, in the process of the invention, is carried out as follow:

Firstly, crude radioactive agent, for example [$^{18}$F]FES, obtained at step ii) is solubilized in an aqueous solution, preferably in an aqueous solution of antioxidant, and fixed on a reversed-phase cartridge.

Then, the reversed-phase cartridge is washed with an aqueous solution, preferably with an aqueous solution of antioxidant, and is then eluted with a polar and organic solvent. Preferably, the solvent is chosen among acetonitrile and ethanol, preferably the eluent is acetonitrile.

This pre-purification allows removing most of unreacted 18-fluorine, solvents and polar compounds such as tetrabutylammonium or K222/K+, carbonate, sulfate and methoxymethyl compound. During this first purification, on the reversed-phase cartridge, the radioactive agent, for example [$^{18}$F]FES, solution, is about 200 times more concentrated than the solution entering the reversed-phase cartridge.

During this step, the concentration of the aqueous solution of antioxidant is at least equal to 0.1% m/v, preferably the concentration of the aqueous solution of antioxidant is comprised between 0.45% and 0.55% m/v. Preferably, the concentration of aqueous solution of antioxidant is equal to 0.5% m/v.

Then, the radioactive agent, for example [$^{18}$F]FES collected from the reversed-phase cartridge undergoes a second purification step by means of a HPLC. This second purification allows removing synthesis impurities and related substances such as estriol formed by hydrolysis of residual precursor.

The HPLC column is preferably a silica C8-C18 column, supporting a pressure up to 200 bars. With this column, precursor, partially-hydrolyzed precursor and the radioactive agent are separated. Preferably, in the case of [$^{18}$F]FES, estradiol, fluoroestradiol, precursor and partially-hydrolyzed precursor are separated.

The eluent used for this step may be any solvent allowing the separation of these compounds. Examples of such eluent preferably include purified water, ethanol, acetonitrile or a mixture of these solvents. In a preferred embodiment of the invention the eluent is preferably a mixture of purified water, acetonitrile and ethanol.

The proportion of the different solvents composing the eluent is preferably chosen in such a way that the separation of the different compounds is effective. In a preferred embodiment the water/acetonitrile/ethanol mass proportion is 55/40/5.

Preferably, the eluent also comprises antioxidant. Preferably, the antioxidant is in solution, preferably in an aqueous solution. The concentration of the solution of antioxidant in water is at least equal to 0.1% m/v, preferably the concentration of the solution of antioxidant is comprised between 0.45% and 0.55% m/v. Preferably, the concentration of antioxidant is equal to 0.5% m/v.

The flow rate of the eluent is preferably fixed and may be comprised between 0.1 and 10 mL/min. In a preferred embodiment, the eluent flow rate is comprised between 3 and 6 mL/min.

During the second purification step, the radioactive agent solution, for example [$^{18}$F]FES solution, is at least 50 times more concentrated than the final solution.

After the second purification on HPLC, the radioactive agent, for example [$^{18}$F]FES, peak, is collected and optionally diluted in aqueous solution of antioxidant. The concentration of the aqueous solution of antioxidant is at least equal to 0.1% m/v, preferably the concentration of the aqueous solution of antioxidant is comprised between 0.45% and 0.55% m/v. Preferably, the concentration of antioxidant is equal to 0.5% m/v.

Then, radioactive agent, for example [$^{18}$F]FES, obtained after HPLC purification is fixed on a second reversed phase cartridge, preferably identical to the first one, in order to remove the HPLC solvents. Reversed phase cartridge is then washed with an aqueous solution, preferably with an aqueous solution of antioxidant.

The concentration of the aqueous solution of antioxidant is at least equal to 0.1% m/v, preferably the concentration of the aqueous solution of antioxidant is comprised between 0.45% and 0.55% m/v. Preferably, the concentration of antioxidant is equal to 0.5% m/v.

During this third purification step, the radioactive agent solution, for example [$^{18}$F]FES solution, is at least 400 times more concentrated than before entering in the cartridge.

Examples of antioxidant preferably used in the invention include ascorbic acid, polyphenols, glutathione, tocopherol, caffeic acid, alkali metal salts or alkaline earth metal salts of ascorbic acid, alone or in admixture.

In a preferred embodiment according to the invention, the antioxidant preferably used includes ascorbic acid, alkali metal salts or alkaline earth metal salts of ascorbic acid, alone or in admixture.

In a preferred embodiment according to the invention, antioxidant is preferably sodium ascorbate. Advantageously sodium ascorbate does not concentrate on cartridges nor preparative HPLC columns.

Then, the reversed phase cartridge on which radioactive agent, for example [$^{18}$F]FES, is fixed is eluted with ethanol. The concentration of ethanol added is preferably inferior to 12% by weight, and preferably inferior to 3% by weight.

Advantageously, by stabilizing the radioactive agent during purification by the antioxidant, the present invention also enables to work with higher concentration of radioactive agent and thus enables advantageously to limit the quantity of solvent used and preferably ethanol. The purification step iii) on cartridge allows advantageously to manage precisely the amount of ethanol in the final solution, comprised between 3% and 15% v/v, preferably between 3% and 10% v/v. Preferably, the amount of ethanol is equal to 3.5% v/v.

It is further possible to formulate the radioactive agent recovered from the purification step. This formulation can be carried out in the presence of antioxidant. Preferably, the formulation step is carried out by adding a saline solution to the product obtained at the end of the purification step, preferably at the end of step iii). The addition of the saline solution enables to prepare an isotonic solution. Preferably, this saline solution comprises antioxidant.

The saline solution is made preferably of any salt compatible with the radioactive agent, for example [$^{18}$F]FES, and intravenous injection, when the radioactive agent is added by intravenous injection. In a preferred embodiment, sodium chloride is used.

The concentration of the saline solution is preferably comprised between 0.8 and 1.0 wt %, preferably the concentration of the saline solution is equal to 0.9 wt %.

The amount of antioxidant added is adjusted allowing stabilization of the compound during this step and preventing radiolysis of the radioactive compound.

The concentration of the aqueous solution of antioxidant used in the formulation step is at least equal to 0.1% m/v, preferably the concentration of the aqueous solution of antioxidant is comprised between 0.4% and 0.5% m/v. Preferably, the concentration of antioxidant is equal to 0.45% m/v.

The solution obtained is a pure radioactive agent stock solution, preferably a pure [$^{18}$F]FES stock solution.

Antioxidant may also be added during the different steps of the radioactive agent synthesis, and not only during the purification step. For example, antioxidant may be added during step (ii). The antioxidant is preferably used in solution, preferably in aqueous solution.

Preferably, the formulation step of the method of the invention is carried out in the presence of an antioxidant. The antioxidant is preferably used in solution, preferably in aqueous solution.

Preferably, the radiolabeling step of the method of the invention is carried out in the presence of an antioxidant; preferably the antioxidant is added during the hydrolysis step. The antioxidant is preferably used in solution, preferably in aqueous solution.

The method of synthesis of the invention, characterized in that antioxidant is at least added during the purification step, allows to better prevent radiolysis of the radioactive agent synthesized, to better stabilize this radioactive agent for a longer time and to limit the quantity of ethanol added during the purification step to limit the concentration of the radioactive agent. Thus, the method of the invention allows to get rid of the disadvantages cited in the prior art.

The present invention also relates to a composition obtained by the method of the invention and preferably comprising a radioactive agent, antioxidant and optionally an excipient. The excipient comprised in the composition comprises saline compound and ethanol.

In a preferred embodiment according to the invention the excipient comprised in the composition preferably comprises between 3 to 15% v/v of ethanol, preferably between 3 to 10% v/v, preferably 3.5% v/v.

In a preferred embodiment according to the invention, the composition preferably comprises from 0.4 to 0.5% m/v of antioxidant and the excipient comprised in the composition preferably comprises:

from 0.8 to 1.0 wt % of a salt, preferably sodium chloride;
from 3 to 15% v/v, preferably 3 to 10% v/v of ethanol.

Advantageously, the process according to the invention enables to obtain a composition comprising a lower ethanol amount than in the composition not obtained by the process of the invention.

In a preferred embodiment according to the invention, the composition preferably comprises 0.45% m/v of antioxidant and the excipient comprised in the composition preferably comprises:

0.9% m/v of a salt;
3.5% by volume of ethanol.

Advantageously, the radioactive composition obtained with the method of the invention, and preferably the [$^{18}$F] FES composition, is characterized by a stability observed during at least 8 hours, preferably during at least 10 hours, and preferably during at least 12 hours.

In a preferred embodiment according to the invention, the radioactive agent solution, for example [$^{18}$F]FES solution, obtained with the method of the invention is preferably characterized by a radiochemical purity at least superior to 95%, preferably at least superior to 97%, preferably at least superior to 98%.

Radiochemical purity is the ratio of the radioactivity of the radionuclide agent under chemical form on the total radioactivity of this same radionuclide.

In a preferred embodiment according to the invention, the total estrogen concentration comprised in the radioactive agent solution, for example [$^{18}$F]FES solution is lower than 1 μg/mL.

In a preferred embodiment according to the invention, the radioactive agent solution, for example [$^{18}$F]FES solution, obtained with the method of the invention is preferably characterized by a pH close to neutrality, preferably comprised between 4 and 8.5, preferably the pH is comprised between 4.5 and 8.

The present invention also relates to a method for preventing radiolysis, preferably self-radiolysis, of a radioactive agent composition comprising the synthesis of said radioactive agent according to the method of the invention. In a preferred embodiment, the method for preventing radiolysis of a radioactive agent comprises the synthesis of said radioactive agent, comprising at least a purification step carried out in the presence of an antioxidant.

EXAMPLES

Abbreviates:
[$^{18}$F]FES: [$^{18}$F] Fluoroestradiol
Precursor: 3-O-methoxymethyl-16,17-O-sulfuryl-16-epi-estriol Example 1 (Comparative): Synthesis of [$^{18}$F]FES without Adding of Antioxidant, Evaluation of the Influence of the Quantity of 18-Fluorine

[$^{18}$F]fluoroestradiol was prepared on two different automatic apparatus, Neptis® of ORA company or All-In-One® of TRASIS company. The skilled person knows how to operate such a cassette-synthetizer in order to carry out the [$^{18}$F]FES synthesis.

18-Fluorine is prepared from $^{18}O(p,n)^{18}F$ reaction in a cyclotron by irradiation with protons of energy comprised between 14 and 18 MeV.

The 18-Fluorine preparation reaction is a classical reaction well-known by the skilled person. Enriched water of CIL®, ROTEM® or ORPHACHEM® companies is used.

From 37 to 450 GBq of 18-Fluorine (equivalent to approximately 10 to 100 ng) previously formed is fixed on a polymeric and carbonated ion-exchange resin. The ion-exchange resin is then eluted by 0.4 to 1 mL of a solution of tetrabutylammonium hydrogenocarbonate with an eluent flow equal to 10 mL/min.

Eluate is transferred into the reactor and dry-evaporated at 95° C. under dried nitrogen. Acetonitrile is added into the reactor. At the end of this step, the temperature is lowered to a temperature comprised between 70 and 80° C.

From 0.5 to 10 mg of precursor in solution in acetonitrile is added and the temperature of the reactor is heated to 130° C. during 10 minutes for radiolabeling. Acetonitrile is partly evaporated during 90 seconds under 90° C.

Hydrolysis of the compound is carried out with a diluted solution of sulfuric acid in ethanol during 5 minutes at 110° C.

After hydrolysis, the reactive media is solubilized in water and fixed on a polymeric reversed-phase cartridge. Unreacted fluorides, solvents, and polar compounds (tetrabutylammonium, carbonate, sulfates, methoxy-methyl) are eliminated by the washing of the cartridge with water, then cartridge is eluted with acetonitrile.

Compound obtained exiting the reversed-phase cartridge is purified in High Pressure Liquid Chromatography (HPLC). The HPLC is characterized by a semi-preparative pump, a silica C8 to C18 column at a temperature comprised between 15 and 25° C.

Eluant is a mixture of purified water/acetonitrile/ethanol (55/40/5). Eluant flow is comprised between 2 and 5 mL/min.

The totality of the $[^{18}F]FES$ peak (from 2 to 8 mL) is collected and diluted in water, before to be fixed on a reversed-phase cartridge, identical to the previous one.

Reversed-phase cartridge is washed with 20 mL of water, and then elution with ethanol is carried out to collect $[^{18}F]FES$ solution which is diluted with isotonic injectable 0.9% m/v sodium chloride solution. $[^{18}F]FES$ stock solution is obtained.

Radiochemical purity of the $[^{18}F]FES$ stock solution is measured.

Several batches with different quantity of 18-Fluorine (QMA, GBq) have been evaluated. Quantity of $[^{18}F]FES$ obtained, decay corrected molar yield and radiochemical purity at the end of the synthesis are measured and/or calculated and given in Table 1.

The decay corrected molar yield is the $[^{18}F]FES$ molar yield at the end of the synthesis corrected by a decay factor, corresponding to the decay of 18-Fluorine used for the synthesis. Decay factor depends on the length of the synthesis.

TABLE 1

$[^{18}F]FES$ obtained, decay corrected molar yield and radiochemical purity at the end of the synthesis without antioxidant.

| Batch | Quantity of 18-Fluorine (GBq) | Quantity of $[^{18}F]FES$ obtained (GBq) | Decay corrected molar yield (%) | Radio-chemical purity (%) |
|---|---|---|---|---|
| 1 | 153.6 | 41.1 | 43.2 | 98.5 |
| 2 | 180.8 | 45.8 | 40.2 | 99.3 |

TABLE 1-continued $[^{18}F]FES$ obtained, decay corrected molar yield and radiochemical purity at the end of the synthesis without antioxidant.

| Batch | Quantity of 18-Fluorine (GBq) | Quantity of $[^{18}F]FES$ obtained (GBq) | Decay corrected molar yield (%) | Radio-chemical purity (%) |
|---|---|---|---|---|
| 3 | 219.2 | 61.2 | 43.7 | 98.3 |
| 4 | 238.0 | 48.8 | 32.1 | 98.9 |
| 5 | 246.0 | 53.4 | 33.8 | 98.4 |
| 6 | 257.8 | 57.1 | 34.9 | 97.2 |
| 7 | 274.0 | 44 | 25.1 | 97.0 |
| 8 | 280.8 | 43.3 | 26.1 | 96.0 |
| 9 | 282 | 48.0 | 29.1 | 95.9 |
| 10 | 480 | 59.1 | 19.3 | 93.0 |

These results show that when the quantity of 18-Fluorine used for the synthesis of $[^{18}F]FES$ increases, the quantity of $[^{18}F]FES$ obtained does not equally increase and thus the decay corrected molar yield of $[^{18}F]FES$ decreases. This shows that the industrially-scale production of $[^{18}F]FES$ without anti-oxidant is difficult because of the degradation (radiolysis) of $[^{18}F]FES$ when produced in high quantity.

Moreover, the radiochemical purity of the different batches decreases when the quantity of 18-Fluorine used for the synthesis increases.

Example 2 (Comparative): Synthesis of $[^{18}F]FES$ with Antioxidant During Purification Steps, without Adding of Antioxidant in the Final Product, Evaluation of the Radiochemical Purity During Storage The beginning of the synthesis (radioelement synthesis and radiolabeling steps) is identical to the one of example 1, except that the quantity of 18-Fluorine is equal to 250 GBq.

After hydrolysis, the reactive media is solubilized in an aqueous 0.5% m/v sodium ascorbate solution and fixed on a polymeric reversed-phase cartridge. Unreacted fluorides, solvents, and polar compounds (tetrabutylammonium, carbonate, sulfates, methoxy-methyl) are eliminated by the washing of the cartridge with an aqueous solution of sodium ascorbate. Then, the cartridge is eluted with acetonitrile.

Compound obtained exiting the reversed-phase cartridge is purified in High Pressure Liquid Chromatography (HPLC). The HPLC is characterized by a semi-preparative pump, a silica C8 to C18 column at a temperature comprised between 15 and 25° C.

Eluent is a solution of 0.5% m/v sodium ascorbate in purified water/acetonitrile/ethanol (55/40/5). Eluent flow is comprised between 2 and 5 mL/min.

The totality of the $[^{18}F]FES$ peak (from 2 to 10 mL) is collected and diluted in a 0.5% m/v aqueous sodium ascorbate solution, before to be extracted on a reversed-phase cartridge, identical to the previous one.

Reversed-phase cartridge is washed with 20 mL of a 0.5% m/v aqueous sodium ascorbate solution, and then eluted with ethanol. Then, $[^{18}F]FES$ solution collected is diluted with isotonic injectable 0.9% m/v sodium chloride solution. $[^{18}F]FES$ stock solution is obtained.

Radiochemical purity at the end of the synthesis, and after 4, 8 and 10 hours of storage is measured and given in table 2.

TABLE 2

Influence of the length of the storage on radiochemical purity, when synthesis is carried out without antioxidant.

| Time of storage (hours) | Radio-chemical purity (%) |
|---|---|
| 0 | 99.3 |
| 4 | 95 |
| 8 | 93 |
| 10 | 92 |

This table shows that the radiochemical purity decreases when the storage length increases. After 10 hours of storage, the radiochemical purity of [$^{18}$F]FES when synthesized without antioxidant is decreased by 7.3%.

Figure 1:
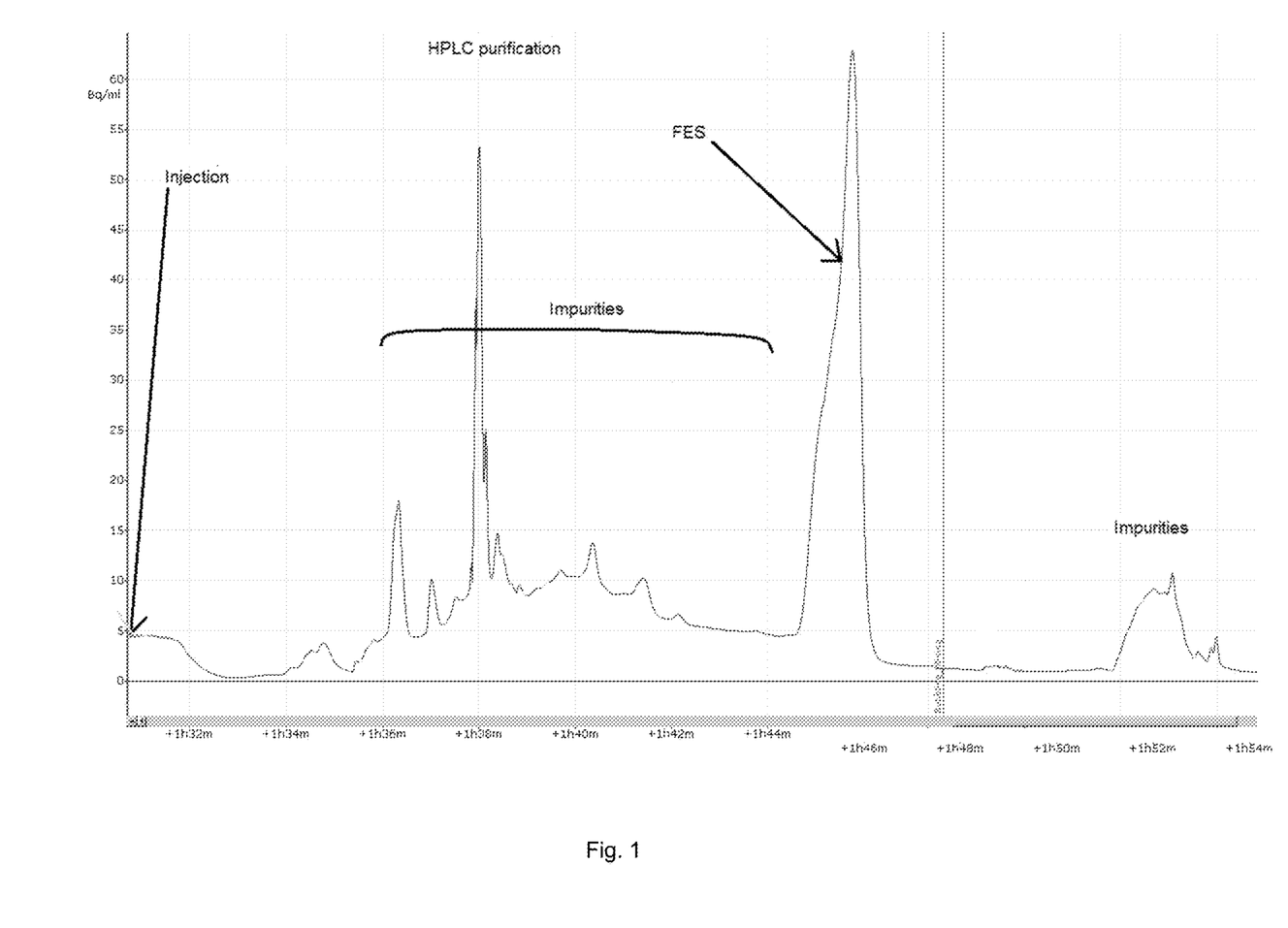
FIG. 1 is a HPLC chromatogram giving the concentration with reference to the retention time of crude [$^{18}$F]FES synthesized without an antioxidant.

The chromatogram of purification of the crude [$^{18}$F]FES is given in FIG. 1.

This figure gives the concentration of the different compounds with reference to the retention time. When no antioxidant is added during the synthesis, the impurities peak is wide and big.

This means that after purification, the crude [$^{18}$F]FES comprises lots of impurities (radioactive or synthesis by-products), and the [$^{18}$F]FES yield is lowered.

Example 3: Synthesis of [$^{18}$F]FES in the Presence of Antioxidant (Sodium Ascorbate), Evaluation of the Influence of the Quantity of 18-Fluorine Steps of radioelement synthesis and radiolabeling are identical to the one of example 1.

After hydrolysis, the reactive media is solubilized in an aqueous 0.5% m/v sodium ascorbate solution and fixed on a polymeric reversed-phase cartridge. Unreacted fluorides, solvents, and polar compounds (tetrabutylammonium, carbonate, sulfates, methoxy-methyl) are eliminated by the washing of the cartridge with an aqueous solution of sodium ascorbate. Then, the cartridge is eluted with acetonitrile.

Compound obtained exiting the reversed-phase cartridge is purified in High Pressure Liquid Chromatography (HPLC). The HPLC is characterized by a semi-preparative pump, a silica C8 to C18 column at a temperature comprised between 15 and 25° C.

Eluant is a solution of 0.5% m/v sodium ascorbate in purified water/acetonitrile/ethanol (55/40/5). Eluant flow is equal comprised between 2 and 5 mL/min.

The totality of the [$^{18}$F]FES peak (from 2 to 10 mL) is collected and diluted in a 0.5% m/v aqueous sodium ascorbate solution, before to be fixed on a reversed-phase cartridge, identical to the previous one.

Reversed-phase cartridge is washed with 20 mL of a 0.5% m/v aqueous sodium ascorbate solution, and then eluted with ethanol. Then, [$^{18}$F]FES solution collected is diluted with isotonic injectable 0.9% m/v sodium chloride solution containing 0.45% m/v sodium ascorbate. [$^{18}$F]FES stock solution is obtained.

Radiochemical purity of the [$^{18}$F]FES stock solution is measured.

Several batches with different quantity of 18-Fluorine (QMA, GBq) have been evaluated. Decay corrected molar yield and radiochemical purity at the end of the synthesis are calculated and given in Table 3.

TABLE 3 quantity of 18-Fluorine (QMA, GBq), decay corrected molar yield and radiochemical purity calculated at the end of the synthesis when carried in the presence of sodium ascorbate.

| Batch number | Quantity of 18-Fluorine (GBq) | Quantity of [$^{18}$F]FES obtained (GBq) | Decay corrected molar yield (%) | Radio-chemical purity (%) | Radio-chemical purity after 10 h storage (%) |
|---|---|---|---|---|---|
| 1 | 79 | 46.7 | 86.4 | 98.8 | 98.0 |
| 2 | 99 | 16.6 | 68.8 | 99.5 | 99.0 |
| 3 | 164 | 78.4 | 69.8 | 98.0 | 96.7 |
| 4 | 195 | 98.9 | 74.1 | 97.5 | 97.1 |

The decay corrected molar yield of [$^{18}$F]FES obtained at the end of reaction when sodium ascorbate is added during all the synthesis step from purification to formulation, is much higher than when the synthesis occurs without antioxidant.

Moreover, this table shows that high quantity of [$^{18}$F]FES may be synthesized with a high yield. Indeed, when compared to table 1, when there is not antioxidant, for the same quantity of 18-Fluorine used, the decay molar yield is doubled.

Example 4: Synthesis of [$^{18}$F]FES in the Presence of Antioxidant (Sodium Ascorbate), Evaluation of the Radiochemical Purity During Storage The synthesis is identical to the one of example 3, except that the quantity of 18-Fluorine is equal to 164 GBq.

Radiochemical purity at the end of the synthesis, and after 5 and 10 hours of storage is measured and given in table 4.

TABLE 4

Influence of the length of the storage on radiochemical purity, when synthesis is carried out in the presence of sodium ascorbate.

| Time of storage (hours) | Radio-chemical purity (%) |
|---|---|
| 0 | 98.0 |
| 5 | 96.8 |
| 10 | 96.7 |

This table shows that the radiochemical purity decreases much less faster when the storage length increases. After 10 hours of storage, the radiochemical purity of [$^{18}$F]FES when synthesized in the presence of sodium ascorbate is decreased by 1.3% (compared to 7.3% when the synthesis is carried out without sodium ascorbate).

Example 5: Synthesis of [$^{18}$F]FES in the Presence of Sodium Ascorbate, Purification Chromatogram The synthesis is identical to the one of example 3, except that the quantity of 18-Fluorine is equal to 260 GBq.

Figure 2:
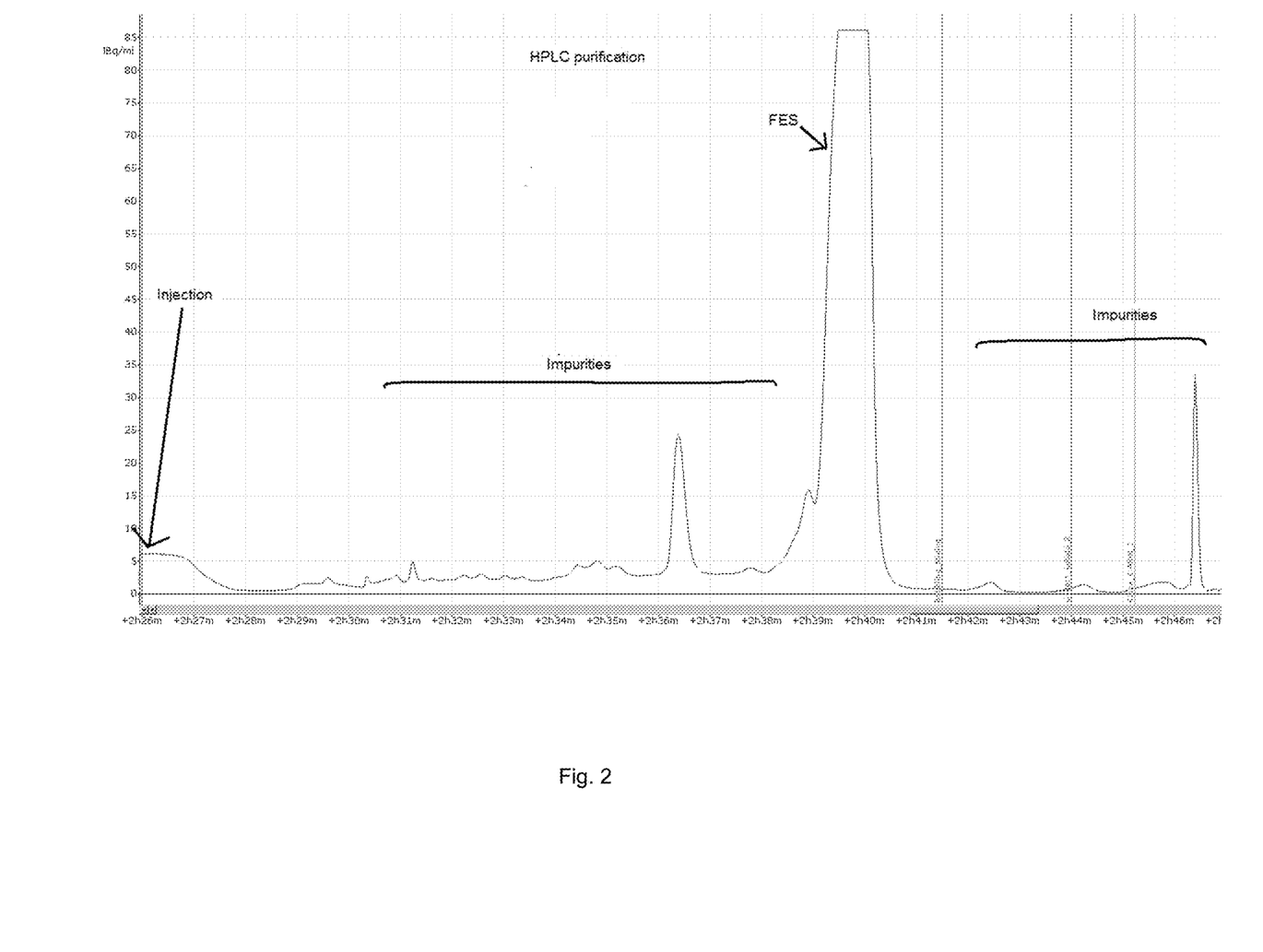
FIG. 2 is a HPLC chromatogram giving the concentration with reference to the retention time of crude [$^{18}$F]FES synthesized in the presence of sodium ascorbate.

The chromatogram of purification of the crude [$^{18}$F]FES obtained when synthesized in the presence of sodium ascorbate is given in FIG. 2.

This figure gives the concentration of the different compounds with reference to the retention time. When sodium ascorbate is added during the synthesis, the impurities and degradation products peak is almost nonexistent.

This means that after purification, the crude FE[$^{18}$F]FES does not comprise as much impurities as when no antioxidant is added during the synthesis and the final yield and the final radiochemical purity are enhanced.

The invention claimed is:
1. A method for the synthesis of a radioactive agent composition, the method comprising:
   i) providing an amount of $^{18}F^-$ with a radioactivity in the range of 79-450 GBq;
   ii) providing a precursor;
   iii) combining the precursor and the $^{18}F^-$, performing nucleophilic substitution, and performing hydrolysis, thereby performing synthesis of 16α-[$^{18}$F]fluoro-17β-estradiol:

wherein the synthesis is performed in the presence of an antioxidant;
   iv) performing at least chromatographic purification of the 16α[$^{18}$F]fluoro-17β-estradiol in the presence of an antioxidant; and
   v) formulating the 16α-[$^{18}$F]fluoro-17β-estradiol with excipient in the presence of an antioxidant to obtain a formulation with 16α-[$^{18}$F]fluoro-17β-estradiol suitable for imaging;
   wherein the synthesis, purification, and formulating are performed in a manner to inhibit radiolysis and provide the 16α-[$^{18}$F]fluoro-17β-estradiol formulation with a radiochemical purity of at least 95% and stability for at least 10 hours, wherein the antioxidant is selected from the group consisting of ascorbic acid, polyphenols, glutathione, tocopherol, caffeic acid, alkali metal salts or alkaline earth metal salts of ascorbic acid.

2. The method according to claim 1 wherein the antioxidant is selected from the group consisting of ascorbic acid, alkali metal salts or alkaline earth metal salts of ascorbic acid.

3. The method according to claim 1 wherein the antioxidant is sodium ascorbate.

4. The method according to claim 1 wherein the antioxidant is added during the synthesis after the hydrolysis in an amount at least equal to 0.1% m/v.

5. The method of claim 1, wherein the chromatographic purification is carried out using HPLC, a reversed-phase cartridge before the HPLC, and a reversed-phase cartridge after the HPLC.

6. The method of claim 5, further comprising using an eluent during the HPLC of 0.5% m/v sodium ascorbate in water/acetonitrile/ethanol (55/40/5).

7. The method of claim 1, wherein:
   the formulation comprises an excipient comprising sodium chloride, sodium ascorbate and ethanol; and
   the formulation comprises no more than 10% v/v ethanol.

8. The method of claim 3, wherein the sodium ascorbate is present in an amount ranging from 0.1% m/v to 0.55% m/v.

9. The method of claim 1, wherein the formulation has a radiochemical purity of at least 95% and stability for at least 12 hours.

10. The method of claim 1, wherein the $^{18}F^-$ is provided in the form of an 18-fluoride-tetrabutylammonium (TBA) complex.

11. The method of claim 10, further comprising reacting the 18-fluoride-TBA complex with the precursor to obtain the 16α[$^{18}$F]fluoro-17β-estradiol.

12. The method of claim 10, wherein the 18-fluoride-TBA complex is prepared using tetrabutylammonium (TBA) carbonate.

13. The method of claim 1, wherein the 16α-[$^{18}$F]fluoro-17β-estradiol is provided with a decay corrected molar yield of at least about 69%.

14. The method of claim 1, wherein the duration of the synthesis is on the order of minutes.

15. A method for the synthesis of a radioactive agent composition, the method comprising:
   obtaining $^{18}F^-$ from irradiated $^{18}O$ water by processing the irradiated $^{18}O$ water with an ion exchange resin cartridge;
   synthesizing 16α-[$^{18}$F]fluoro-17β-estradiol by combining the $^{18}F^-$ with a precursor in acetonitrile, performing hydrolysis, and adding sodium ascorbate;
   processing the 16α-[$^{18}$F]fluoro-17β-estradiol with a first reversed-phase cartridge, then HPLC, then with a second reversed-phase cartridge, each performed in the presence of sodium ascorbate; and
   formulating an intravenous injectable solution of the 16α-[$^{18}$F]fluoro-17β-estradiol comprising sodium ascorbate and ethanol.

16. A method for the synthesis of a radioactive agent composition, the method comprising:
   a) synthesis of 16α-[$^{18}$F]fluoro-17β-estradiol by:
      forming an 18-fluoride-tetrabutylammonium (TBA) complex from $^{18}F^-$ and tetrabutylammonium (TBA) carbonate;
      performing a nucleophilic substitution reaction with a precursor and the 18-fluoride-tetrabutylammonium (TBA) complex to obtain a fluorinated product; and
      hydrolyzing the fluorinated product to obtain 16α-[$^{18}$F] fluoro-17β-estradiol and dilution with an aqueous solution of sodium ascorbate;
   b) purification of the 16α-[$^{18}$F]fluoro-17β-estradiol by:
      performing a pre-HPLC purification and washing with an aqueous solution of sodium ascorbate;
      performing high pressure liquid chromatography (HPLC) with an eluent comprising sodium ascorbate and ethanol; and
      collecting the 16α-[$^{18}$F]fluoro-17β-estradiol and diluting in an aqueous solution of sodium ascorbate;
   c) formulation of a composition comprising the 16α-[$^{18}$F] fluoro-17β-estradiol by:
      removing HPLC solvent by performing post-HPLC purification, washing with an aqueous solution of sodium ascorbate, and eluting with ethanol; and
      diluting with sodium chloride containing sodium ascorbate to obtain the 16α-[$^{18}$F]fluoro-17β-estradiol in an isotonic solution.

17. The method of claim 1, wherein the formulation is adapted for imaging estrogen receptors and/or adapted for detecting breast cancer.

18. The method of claim 1, wherein the precursor has the structure:

19. The method of claim 1, wherein the synthesis, purification and formulating are performed in an automatic cassette-type synthesizer.